United States Patent
Trieselmann et al.

(10) Patent No.: US 11,319,310 B2
(45) Date of Patent: May 3, 2022

(54) HETEROCYCLYL-SUBSTITUTED OXADIAZOLOPYRIDINE DERIVATIVES FOR USE AS GHRELIN O-ACYL TRANSFERASE (GOAT) INHIBITORS

(71) Applicant: Boehringer Ingelheim International GmbH, Ingelheim am Rhein (DE)

(72) Inventors: Thomas Trieselmann, Mettenberg (DE); Cedrickx Godbout, Attenweiler (DE); Viktor Vintonyak, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 164 days.

(21) Appl. No.: 16/966,489

(22) PCT Filed: Jan. 28, 2019

(86) PCT No.: PCT/EP2019/051993
§ 371 (c)(1),
(2) Date: Jul. 31, 2020

(87) PCT Pub. No.: WO2019/149659
PCT Pub. Date: Aug. 8, 2019

(65) Prior Publication Data
US 2021/0040077 A1    Feb. 11, 2021

(30) Foreign Application Priority Data
Feb. 2, 2018  (EP) .................................. 18154828

(51) Int. Cl.
*C07D 413/14* (2006.01)
(52) U.S. Cl.
CPC .................. *C07D 413/14* (2013.01)
(58) Field of Classification Search
None
See application file for complete search history.

(56) References Cited

U.S. PATENT DOCUMENTS

2015/0018547 A1    1/2015  Takakura et al.

FOREIGN PATENT DOCUMENTS

| WO | 2004082383 | 8/2013 |
|---|---|---|
| WO | 2013125732 A1 | 8/2013 |
| WO | 2013192388 | 12/2013 |
| WO | 2015073281 A1 | 5/2015 |
| WO | 2016044467 | 3/2016 |
| WO | 2016123275 | 8/2016 |
| WO | 2016168222 | 10/2016 |
| WO | 2016168225 | 10/2016 |
| WO | 2018024653 | 2/2018 |

OTHER PUBLICATIONS

International Search Authority and Written opinion, for PCT/EP2017/069274, dated Sep. 15, 2017.
Kuppens, "Elelvated Ration of acylated to unacylated ghrelin in children and yoiung adults with Prader-Willi syndrome", Endocrine, Humana Press, vol. 50, No. 3, 2015, p. 633-642.
Vasil. Russian Chem Bulletin, Reactions of cyanoturazans with [beta]-dicarbonyl compiunds, 2001, vol. 50, p. 1280-1286.
Hirozane, SLAS Discovery, Identification and Characterization of a new series of Ghrelin O-Acyl Transferase Inhibitors, vol. 23, 2018.
Vasil, Mendellev Communications, Effective Synthesis of Funtionalized furazano, 1994, vol. 2, p. 57-58.

*Primary Examiner* — Heidi Reese
(74) *Attorney, Agent, or Firm* — David L. Kershner

(57) ABSTRACT

The present invention relates to compounds of general formula (I) wherein the variables X, $R^1$, n, p and q are defined as in claim 1, which have valuable pharmacological properties, in particular bind to ghrelin O-acyl transferase (GOAT) and modulate its activity. The compounds are suitable for treatment and prevention of diseases which can be influenced by this receptor, such as metabolic diseases, in particular obesity.

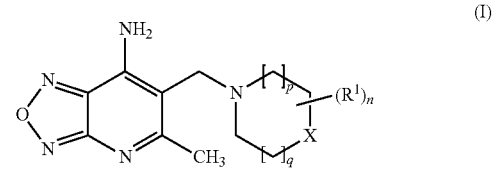

16 Claims, No Drawings

HETEROCYCLYL-SUBSTITUTED OXADIAZOLOPYRIDINE DERIVATIVES FOR USE AS GHRELIN O-ACYL TRANSFERASE (GOAT) INHIBITORS

FIELD OF THE INVENTION

The present invention relates to novel oxadiazolopyridine derivatives, that are inhibitors of the ghrelin O-acyl transferase (GOAT), to processes for their preparation, to pharmaceutical compositions containing these compounds and to their medical use for the prophylaxis and/or treatment of diseases which can be influenced by the modulation of the function of the ghrelin O-acyl transferase (GOAT). Particularly, the pharmaceutical compositions of the invention are suitable for the prophylaxis and/or therapy of metabolic diseases, such as obesity, including, but not limited to obesity in patients suffering from Prader-Willi-Syndrome (PWS), insulin resistance and diabetes, particularly type 2 diabetes.

BACKGROUND OF THE INVENTION

Ghrelin O-Acyltransferase (GOAT) is a member of the membrane-bound O-acyl transferase (MBOAT) protein family, and the only enzyme in humans capable of promoting an acylation reaction on the peptide hormone ghrelin. By linking a medium-chain fatty acid to the Serine-3 position of the 28-amino acid peptide, GOAT converts unacylated ghrelin (UAG) to acylated ghrelin (AG) which is the natural ligand of the ghrelin receptor GHSR1a (growth hormone secretagogue receptor 1a). The ghrelin receptor is expressed in various areas of the brain involved in energy homeostasis. Activation of the receptor by AG results in stimulation of neuronal pathways leading to increased food intake, fat deposition and weight gain thus linking the ghrelin system to obesity. In humans, AG in plasma peaks immediately before mealtimes and drops in response to food intake (D. E. Cummings et al., Diabetes (2001) 50(8), 1714-1719). Infusion of AG has been shown to increase food intake in lean and obese subjects (M. R. Druce et al., Int. J. Obes. (2005), 29(9), 1130-1136). So far no receptor has been identified for UAG, but it has been shown to have functional antagonistic effects to AG at least with respect to its metabolic properties (W. Zhang et al., Endocrinology (2008) 149 (9), 4710-4716). Since an inhibitor of GOAT would substantially diminish the level of the GHSR1a ligand AG and concomitantly increase the functional antagonist UAG, it would be useful for the treatment of obesity as an adjunct to a reduced-calorie diet and increased physical activity for chronic weight management.

Insatiable hunger and severe obesity are characteristic features of the Prader-Willi-Syndrome (PWS), a genetically caused orphan disease with a complex pathology. AG levels in plasma of PWS subjects are elevated and AG/UAG ratios are increased suggesting a causal relationship (N. Wierup et al., Regulatory Peptides (2002) 107, 63-69; R. J. Kuppens et al., Endocrine (2015) 50(3), 633-642). Therefore GOAT inhibitors may be effective in reducing food craving behavior and body weight in PWS patients ameliorating one major burden affecting the patients and their families.

Furthermore the ghrelin system seems to play a major role in glucose homeostasis. Administration of AG to human subjects leads to suppression of glucose-induced insulin secretion and an increase in plasma glucose. Infusion of UAG is able to counteract the hyperglycemic effect of AG (F. Broglio et al., J. Clin. Endocrinol. Metab. (2004) 89, 3062-3065). The expression of GOAT, ghrelin and GHSR1a in human pancreatic islets suggests a paracrine role on insulin secretion (A. DelParigi et al., J. Clin. Endocrinol. Metab. (2002) 87(12), 5461-5464). In addition UAG promotes pancreatic β-cell and human islet cell survival in vitro (R. Granata et al., Endocrinology (2007) 148(2), 512-529) and prevents diabetes in streptozotocin treated rats (R. Granata et al., J. Med. Chem. (2012) 55(6), 2585-2596). Thus treatment with a GOAT inhibitor is expected to improve glucose homeostasis in patients with type 2 diabetes or obese with impaired glucose tolerance.

OBJECT OF THE PRESENT INVENTION

The object of the present invention is to provide new compounds, hereinafter described as compounds of formula I, in particular new oxadiazolopyridine derivatives, which are active with regard to the ghrelin O-acyl transferase (GOAT), notably they are ghrelin O-acyl transferase (GOAT) inhibitors.

A further object of the present invention is to provide new compounds, in particular oxadiazolopyridine derivatives, which have an inhibiting effect on ghrelin O-acyl transferase (GOAT) in vitro and/or in vivo and possess suitable pharmacological and pharmacokinetic properties to use them as medicaments.

A further object of the present invention is to provide effective ghrelin O-acyl transferase (GOAT) inhibitors, in particular for the treatment of metabolic disorders, for obesity, including, but not limited to obesity in patients suffering from Prader-Willi-Syndrome (PWS), insulin resistance and diabetes, in particular type 2 diabetes mellitus.

A further object of the present invention is to provide methods for treating a disease or condition mediated by the inhibition of ghrelin O-acyl transferase (GOAT) in a patient.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

Ghrelin O-acyl transferase (GOAT) inhibitors are known in the art, see for example the compounds disclosed in WO 2013/125732 and WO 2015/073281. The oxadiazolopyridine derivatives of the present invention are structurally quite different and may provide several advantages, such as enhanced potency, high metabolic and/or chemical stability, high selectivity and tolerability, enhanced solubility, the ability to cross the blood-brain barrier and the possibility to form stable salts.

SUMMARY OF THE INVENTION

In a first aspect, the invention relates to a compound of formula

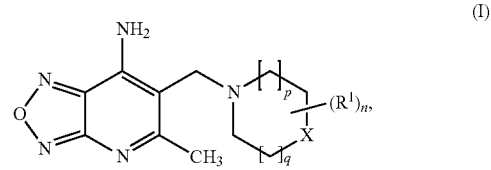

wherein
a) if p is 1 and q is 1, then X is $C(R^2)_2$, O or $NR^3$; or
b) if p is 0 and q is 0, then X is $CHR^1$; or
c) if p is 1 and q is 0, then X is $CR^1R^2$;
and, in any of the above-mentioned cases,
n is an integer selected from 0, 1, or 2;
$R^1$ is independently selected from the group $R^1$-G1 consisting of H, F, CN, $C_{1-3}$-alkyl and phenyl,
  wherein any alkyl group is optionally substituted with 1 or more F atoms, and
  wherein the phenyl group is optionally substituted with 1 or more F atoms or with one $CF_3$ group;
$R^2$ is independently selected from the group $R^2$-G1 consisting of H, F, CN, $C_{1-3}$-alkyl, —OH, —O—$C_{1-4}$-alkyl, —O-pyridinyl and —$SO_2$—($C_{1-3}$-alkyl),
  wherein each alkyl group is optionally substituted with 1 or more F atoms or with one OH group, and
  wherein the pyridinyl group is optionally substituted with a $CH_3$ group;
$R^3$ is selected from the group $R^3$-G1 consisting of —$SO_2$—($C_{1-3}$-alkyl), —$SO_2$—($C_{3-7}$-cycloalkyl), —C(═O)—($C_{1-3}$-alkyl), —C(═O)—($C_{3-7}$-cycloalkyl), —C(═O)—O—($C_{1-6}$-alkyl), and $C_{1-3}$-alkyl,
  wherein each alkyl group is optionally substituted with 1 or more F atoms;
wherein each of the above-mentioned alkyl groups may be substituted with one or more F;
the isoforms, tautomers, stereoisomers, metabolites, prodrugs, solvates, hydrates, and the salts thereof, particularly the physiologically acceptable salts thereof with inorganic or organic acids or bases, or the combinations thereof.

The extension -Gn used within the definitions is meant to identify genus n of the respective substituent. For example, R-G1 defines genus 1 of the substituent R.

The expression "optionally substituted with 1 or more F atoms" means that none or one up to successively all H atoms bound to carbon atoms of the respective group or submoiety may be replaced by F atoms, preferably 1 to 5H atoms or, more preferred, 1 to 3H atoms may be replaced by F atoms.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by inhibiting ghrelin O-acyl transferase (GOAT) in a patient in need thereof characterized in that a compound of general formula I or a pharmaceutically acceptable salt thereof is administered to the patient.

According to another aspect of the invention, there is provided a method for treating a metabolic disease or disorder, such as obesity, including, but not limited to obesity in patients suffering from Prader-Willi-Syndrome, insulin resistance and diabetes, in particular type 2 diabetes mellitus, in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the inhibition of ghrelin O-acyl transferase (GOAT) in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which are mediated by the inhibition of ghrelin O-acyl transferase (GOAT).

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly X, $R^1$, $R^2$, $R^3$, n, p and q are defined as above and hereinafter. If residues, substituents, or groups occur several times in a compound, such as $R^1$ and $R^2$, they may have the same or different meanings. Some preferred meanings of individual groups and substituents of the compounds according to the invention will be given hereinafter. Any and each of these definitions may be combined with each other.

p and q

The indices p and q are each an integer selected from 0 and 1, with the proviso that q cannot be 1, if p is 0.

In one embodiment, p is 1 and q is either 0 or 1.

Preferably, p is 1 and q is 0.

More preferably, p and q are each 1.

In another embodiment, p and q are each 0.

X:

If p and q are both 1, X is selected from one of the following groups ending with "a":

X-G1a:

Provided that p and q are both 1, the group X is preferably selected from the group X-G1a consisting of $C(R^2)_2$, O and $NR^3$.

X-G2a:

Provided that p and q are both 1, in one embodiment, the group X is selected from the group X-G2a consisting of $C(R^2)_2$, and $NR^3$.

X-G3a:

Provided that p and q are both 1, in one embodiment, the group X is selected from the group X-G3a consisting of $C(R^2)_2$.

X-G4a:

Provided that p and q are both 1, in one embodiment, the group X is selected from the group X-G4a consisting of $NR^3$.

In Case q is 0, X is Selected from One of the Following Groups X-G1b and X-G1c:

X-G1b:

If p and q are both 0, the group X is selected from the group X-G1b consisting of $CHR^1$ with the proviso that $R^1$ is not H.

X-G1c:

If p is 1 and q is 0, the group X is selected from the group X-G1c consisting of $CR^1R^2$, with the proviso that at least one of $R^1$ and $R^2$ is not H.

n

The index n is an integer selected from 0, 1 and 2.
Preferably, n is 1 or 2.
More preferably, n is 2.
Most preferably, n is 1.
In another embodiment, n is 0.

$R^1$:

$R^1$-G1:

The group $R^1$ is preferably selected from the group $R^1$-G1 as defined hereinbefore.

$R^1$-G1a:

In one embodiment, the group $R^1$ is independently selected from the group $R^1$-G1a consisting of F, $C_{1-3}$-alkyl and phenyl,
wherein any alkyl group is optionally substituted with 1 or more F atoms; and
wherein the phenyl group is optionally substituted with 1 or more F atoms or with one $CF_3$ group.

$R^1$-G2:

In another embodiment, the group $R^1$ is selected from the group $R^1$-G2 consisting of H, F, methyl and phenyl,
wherein the methyl group is optionally substituted with 1 to 3 F atoms,
and wherein the phenyl group is optionally substituted with 1 to 3 F atoms or with one $CF_3$ group.

$R^1$-G2a:

In another embodiment, the group $R^1$ is selected from the group $R^1$-G2a consisting of F, methyl and phenyl,
wherein any methyl and phenyl group is optionally substituted with 1 to 3 F atoms.

$R^1$-G3:

In another embodiment, the group $R^1$ is selected from the group $R^1$-G3 consisting of H, F, methyl and phenyl,
wherein any methyl group is optionally substituted with 1 to 3 F atoms,
and wherein the phenyl group is optionally substituted with 1 to 3 F atoms or with one $CF_3$ group.

$R^1$-G3a:

In another embodiment, the group $R^1$ is selected from the group $R^1$-G3a consisting of F, methyl and phenyl,
wherein any methyl and phenyl group is optionally substituted with 1 to 3 F atoms.

$R^1$-G4:

In another embodiment, the group $R^1$ is selected from the group $R^1$-G4 consisting of H, F, $CH_3$, $CF_3$ and phenyl,
wherein the phenyl group is optionally substituted with 1 F atom or with 1 $CF_3$ group.

$R^1$-G4a:

In another embodiment, the group $R^1$ is selected from the group $R^1$-G4a consisting of F, $CH_3$, $CF_3$ and phenyl,
wherein the phenyl group is optionally substituted with 1 F atom.

$R^1$-G5:

In another embodiment, the group $R^1$ is selected from the group $R^1$-G5 consisting of H, F, $CH_3$, $CF_3$, 4-fluoro-phenyl and 3-trifluoro-phenyl.

$R^1$-G5a:

In another embodiment, the group $R^1$ is selected from the group $R^1$-G5a consisting of F, $CH_3$, $CF_3$ and 4-fluoro-phenyl.

$R^1$-G6:

In another embodiment, the group $R^1$ is selected from the group $R^1$-G6 consisting of H, F, $CF_3$ and 3-trifluoro-phenyl.

$R^1$-G6a:

In another embodiment, the group $R^1$ is selected from the group $R^1$-G6a consisting of F, $CH_3$ and $CF_3$.

$R^2$:

$R^2$-G1:

The group $R^2$ is preferably selected from the group $R^2$-G1 as defined hereinbefore.

$R^2$-G1a:

In one embodiment, the group $R^2$ is independently of each other selected from the group $R^2$-G1a consisting of H, F, CN, $C_{1-3}$-alkyl, $—O—C_{1-4}$-alkyl and $—SO_2—(C_{1-3}$-alkyl),
wherein each alkyl group is optionally substituted with 1 or more F atoms.

$R^2$-G2:

In another embodiment, the group $R^2$ is independently of each other selected from the group $R^2$-G2 consisting of H, F, CN, $CH_3$, $—CH(CH_3)_2$, OH, $—O—CH_3$, —O-pyridin-4-yl and $—SO_2—CH_3$,
wherein each $CH_3$ group is optionally substituted with 1 to 3 F atoms,
and wherein the isopropyl group is optionally substituted with one OH group,
and wherein the pyridinyl group is optionally substituted with 1 $CH_3$ group.

$R^2$-G2a:

In another embodiment the group $R^2$ is independently of each other selected from the group $R^2$-G2a consisting of H, F, CN, $CH_3$, $—O—CH_3$ and $—SO_2—CH_3$,
wherein each $CH_3$ group is optionally substituted with 1 to 3 F atoms.

$R^2$-G3:

In another embodiment the group $R^2$ is independently of each other selected from the group $R^2$-G3 consisting of H, F, CN, $CH_3$, OH, $—O—CH_3$, —O-(2-methyl-pyridin-4-yl) and $—SO_2—CH_3$,
wherein each $CH_3$ group is optionally substituted with 1 to 3 F atoms.

$R^2$-G3a:

In another embodiment the group $R^2$ is independently of each other selected from the group $R^2$-G3a consisting of H, F, CN, $CH_3$, $—O—CH_3$ and $—SO_2—CH_3$,
wherein each $CH_3$ group is optionally substituted with 1 to 3 F atoms.

$R^2$-G4:

In another embodiment the group $R^2$ is independently of each other selected from the group $R^2$-G4 consisting of H, F, CN, $CH_3$, $CHF_2$, $CF_3$, OH, $—O—CH_3$, $—O—CF_3$ and $—SO_2—CH_3$.

$R^2$-G4a:

In another embodiment the group $R^2$ is independently of each other selected from the group $R^2$-G4a consisting of H, F, CN, $CH_3$, $CHF_2$, $CF_3$, $—O—CH_3$, $—O—CF_3$ and $—SO_2—CH_3$.

$R^2$-G5:

In another embodiment the group $R^2$ is independently of each other selected from the group $R^2$-G5 consisting of H, F, CN, $CH_3$, $CHF_2$, $CF_3$, $—O—CF_3$ and $—SO_2—CH_3$.

R²-G6:

In another embodiment the group R² is independently of each other selected from the group R²-G6 consisting of H, F, CF₃, —C(OH)(CH₃)₂, OH and —O-(2-methyl-pyridin-4-yl).

R³:

R³-G1:

The group R³ is preferably selected from the group R³-G1 as defined hereinbefore.

R³-G2:

In one embodiment, the group R³ is selected from the group R³-G2 consisting of —SO₂—CH₃, —SO₂-cyclopropyl, —C(=O)—CH₃, —C(=O)-cyclopropyl and —C(=O)—O—(C₁₋₄-alkyl), wherein each alkyl group is optionally substituted with 1 to 3 F atoms.

R³-G3:

In another embodiment, the group R³ is selected from the group R³-G3 consisting of —SO₂—CH₃, —SO₂—CHF₂, —SO₂—CF₃, —SO₂-cyclopropyl, —C(=O)—CH₃, —C(=O)—CF₃, —C(=O)-cyclopropyl, —C(=O)—O—CH₃ and —C(=O)—O—(C(CH₃)₃.

R³-G4:

In another embodiment, the group R³ is selected from the group R³-G4 consisting of —SO₂—CH₃, —SO₂—CHF₂, —SO₂—CF₃, —SO₂-cyclopropyl, —C(=O)—CF₃, —C(=O)-cyclopropyl, —C(=O)—O—CH₃ and —C(=O)—O—(C(CH₃)₃.

The following preferred embodiments of compounds of the formula I are described using generic formulae I.1 to I.11, wherein any tautomers, solvates, hydrates and salts thereof, in particular the pharmaceutically acceptable salts thereof, are encompassed. R¹, R², and R³ and n are as defined in this application. If residues, substituents, or groups occur several times in a compound, such as R¹ and R², they may have the same or different meanings.

Examples of preferred subgeneric embodiments (E) according to the present invention are set forth in the following table 1, wherein each substituent group of each embodiment is defined according to the definitions set forth hereinbefore and wherein all other substituents of the formulae I, I.1, I.2, I.3, I.4, I.5, I.6, I.7, I.8, I.9, I.10 and I.11 are defined according to the definitions set forth hereinbefore. For example, the entry -G1 in the column under R- and in the line of E1 means that in embodiment E1 substituent R is selected from the definition designated R-G1. The same applies analogously to the other variables incorporated in the general formulae.

TABLE 1

| E | formula | X | R¹- | R²- | R³- | n | p | q |
|---|---|---|---|---|---|---|---|---|
| E1 | I | -G1a | -G1a | -G1a | -G1 | 0, 1 or 2 | 1 | 1 |
| E2 | I | -G1a | -G1a | -G1a | -G1 | 0 or 1 | 1 | 1 |
| E3 | I | -G1a | -G1a | -G1a | -G1 | 1 | 1 | 1 |
| E4 | I | -G1a | — | -G1a | -G1 | 0 | 1 | 1 |
| E5 | I | -G1a | -G3a | -G3a | -G3 | 0 or 1 | 1 | 1 |
| E6 | I | -G2a | -G1a | -G1a | -G1 | 0, 1 or 2 | 1 | 1 |
| E7 | I | -G2a | -G1a | -G1a | -G1 | 0 or 1 | 1 | 1 |
| E8 | I | -G2a | -G2a | -G2a | -G2 | 0 or 1 | 1 | 1 |
| E9 | I | -G2a | -G3a | -G3a | -G3 | 0 or 1 | 1 | 1 |
| E10 | I | -G2a | -G4a | -G4a | -G4 | 0 or 1 | 1 | 1 |
| E11 | I | -G2a | -G5a | -G5 | -G4 | 0 or 1 | 1 | 1 |
| E12 | I | -G2a | -G6a | -G5 | -G4 | 0 or 1 | 1 | 1 |
| E13 | I | -G3a | -G1a | -G1a | — | 0, 1 or 2 | 1 | 1 |
| E14 | I | -G3a | -G2a | -G2a | — | 0 or 1 | 1 | 1 |
| E15 | I | -G3a | -G3a | -Gea | — | 0 or 1 | 1 | 1 |
| E16 | I | -G3a | -G4a | -G4a | — | 0 or 1 | 1 | 1 |
| E17 | I | -G3a | -G5a | -G5 | — | 0 or 1 | 1 | 1 |
| E18 | I | -G3a | -G6a | -G5 | — | 0 or 1 | 1 | 1 |
| E19 | I | -G4a | -G1a | — | -G1 | 0 or 1 | 1 | 1 |
| E20 | I | -G4a | -G2a | — | -G2 | 0 or 1 | 1 | 1 |
| E21 | I | -G4a | -G3a | — | -G3 | 0 or 1 | 1 | 1 |
| E22 | I | -G4a | -G4a | — | -G4 | 0 or 1 | 1 | 1 |
| E23 | I | -G4a | -G5a | — | -G4 | 0 or 1 | 1 | 1 |
| E24 | I | -G4a | -G6a | — | -G4 | 0 or 1 | 1 | 1 |
| E25 | I | -G1c | -G1 | -G1 | — | 0, 1 or 2 | 1 | 0 |
| E26 | I | -G1c | -G2 | -G2 | — | 0 or 1 | 1 | 0 |
| E27 | I | -G1c | -G3 | -G3 | — | 0 or 1 | 1 | 0 |
| E28 | I | -G1c | -G4 | -G4 | — | 0 or 1 | 1 | 0 |
| E29 | I | -G1c | -G5 | -G6 | — | 0 or 1 | 1 | 0 |
| E30 | I | -G1c | -G6 | -G6 | — | 0 or 1 | 1 | 0 |

Another embodiment concerns those compounds of formula

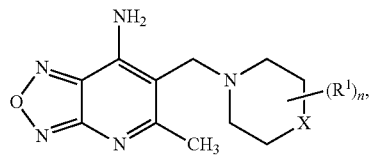
(I.1)

wherein

X is selected from the group consisting of $C(R^2)_2$, and $NR^3$;

n is 0;

the groups $R^2$ are independently selected from the group consisting of: H, F, CN, $CH_3$, $CHF_2$, $CF_3$, —O—$CF_3$ and —$SO_2$—$CH_3$; and $R^3$ is selected from the group consisting of —$SO_2$—$CH_3$, —$SO_2$—$CHF_2$, —$SO_2$—$CF_3$, —$SO_2$— cyclopropyl, —C(=O)—$CF_3$, —C(=O)-cyclopropyl, —C(=O)—O—$CH_3$ and —C(=O)—O—$(C(CH_3)_3)$;

or a salt thereof, particularly a pharmaceutically acceptable salt thereof.

Still another embodiment concerns those compounds of formula

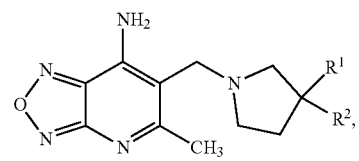
(I.11)

wherein $R^1$ is selected from the group consisting of H, F, $CF_3$ and 3-trifluoro-phenyl; and $R^2$ is selected from the group consisting of H, F, $CF_3$, —C(OH)$(CH_3)_2$, OH and —O-(2-methyl-pyridin-4-yl);

with the proviso that at least one of $R^1$ and $R^2$ is not H;

or a salt thereof, particularly a pharmaceutically acceptable salt thereof.

Preferred compounds of the invention include:

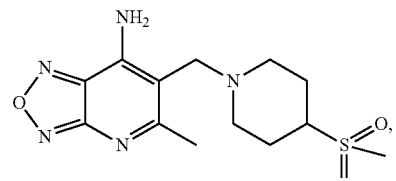

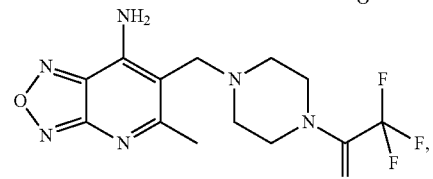

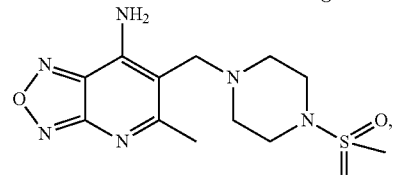

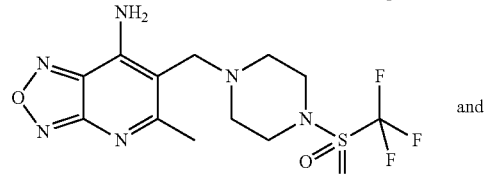

and

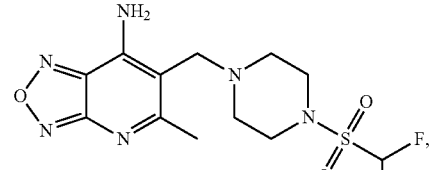

or a salt thereof, particularly a pharmaceutically acceptable salt thereof.

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis, for example.

Moreover, the invention provides processes for making a compound of Formula I.

Optimal reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel, HPLC and/or by recrystallization. The examples which follow are illustrative and, as one skilled in the art will recognize, particular reagents or conditions could be modified as needed for individual compounds without undue experimentation. Starting materials and intermediates used in the methods below are either commercially available or easily prepared from commercially available materials by those skilled in the art.

A compound of Formula I may be made by the methods outlined in Schemes 1 and 2:

Scheme 1

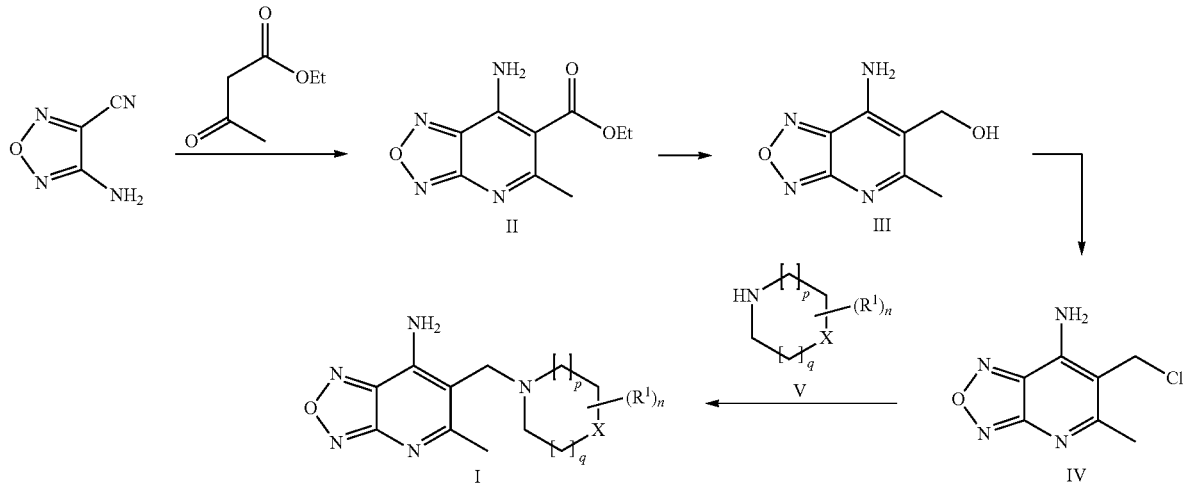

As illustrated in Scheme 1, the reaction of ethyl acetoacetate with 4-amino-1,2,5-oxadiazole-3-carbonitrile (Chemistry of Heterocyclic Compounds (New York, N.Y., United States), 1994, vol. 30, #5 p. 608-611) in the presence of a suitable Lewis acid such as tin (IV) chloride, in a suitable solvent such as toluene or benzene, provides ester II.

Reduction of the ester II with the reducing agent such as sodium bis(2-methoxyethoxy)aluminiumhydride (Red-Al®) or lithium aluminium hydride, in a suitable solvent such as a toluene/tetrahydrofuran mixture, provides alcohol III. Alcohol III can be converted into the corresponding chloride derivative IV using suitable reagents and solvents, such as thionylchloride in dimethylformamide.

Reaction of a substituted heterocyclic amine derivative of formula V with the compound of formula IV in the presence of a suitable base such as N,N-diisopropylethylamine, in a suitable solvent such as N-methylpyrrolidine, provides a compound of formula I.

Scheme 2

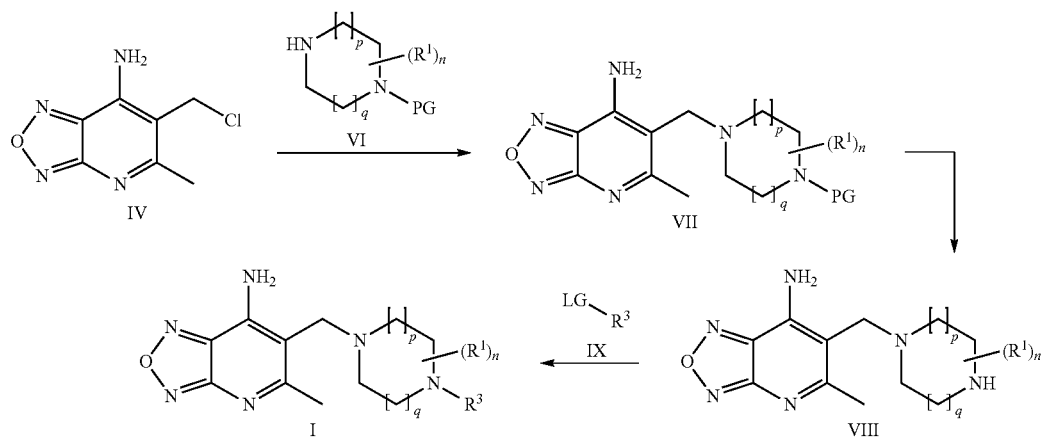

As illustrated in Scheme 2, the reaction of the chloride derivative IV with a substituted heterocyclic amine derivative VI containing a suitable N-protecting group (PG), such as tert-butoxycarbonyl, in the presence of a suitable base such as N,N-diisopropylethylamine, in a suitable solvent such as N-methylpyrrolidine, provides N-protected heterocyclic amine derivative VII. Deprotection of derivative VII with a suitable reagent such as trifluoro acetic acid in a suitable solvent such as dichloromethane provides a deprotected heterocyclic amine derivative VIII. Reaction of VIII with a reagent IX containing a suitable leaving group (LG), such as chloride, in the presence of a suitable base such as N,N-diisopropylethylamine, in a suitable solvent such as dichloromethane, provides compound I.

Further modifications of compounds of formula I by methods known in the art and illustrated in the Examples below may be used to prepare additional compounds of the invention.

The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis for example in "Protecting Groups, $3^{rd}$ Edition", Philip J. Kocienski, Thieme, 2005 or "Greene's Protective Groups in Organic Synthesis, 4th Edition", Peter G. M. Wuts, Theadora W. Greene, John Wiley and Sons, 2007.

The compounds of general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making pharmaceutically acceptable acid or base salts thereof. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The compounds according to the invention are advantageously also obtainable using the methods described in the examples that follow, which may also be combined for this purpose with methods known to the skilled man from the literature.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the inhibition of the ghrelin O-acyl transferase (GOAT) with one or more compounds of the present invention.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

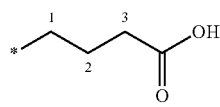

wherein the carboxy group is attached to the third carbon atom of the propyl group.

The terms "1-methylpropyl-", "2,2-dimethylpropyl-" or "cyclopropylmethyl-" group represent the following groups:

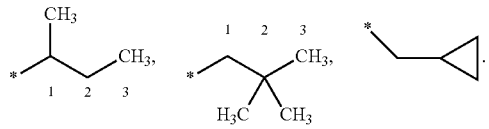

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)— and —C(CH$_3$)(CH$_2$CH$_3$)—.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes —CH=CH$_2$, —CH=CH—CH$_3$, —CH$_2$—CH=CH$_2$.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes —C≡CH, —C≡C—CH$_3$, —CH$_2$—C≡CH.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc.

Many of the terms given above may be used repeatedly in the definition of a formula or group and in each case have one of the meanings given above, independently of one another.

Pharmacological Activity

Determination of hGOAT Activity in HEK293 Cells after Incubation with Test Compound Principle:

HEK293 cells stably transfected with two expression vectors, one coding for preproghrelin cDNA and a second for the expression of human GOATcDNA are used as a cellular model. After feeding the cells with octanoic acid for 5 hours, acyl-ghrelin is measured in cell culture medium by an ELISA procedure.

Materials:
Cellline: Hek293 hGOAT/PPGhrl Clone #1B8 Sodium octanoate, Sigma, Cat.-No. C5038
BSA: Sigma, Cat.-No. A8806
BD Poly-D-Lysin 384-well Plates, black-clear polystyrene BD Bioscience Cat.-No. 356697348-well ELISA human acylated Ghrelin Kit purchased from Bertin Pharman (detailed composition of buffers e.g. wash-puffer, ELISA buffer not known) All further reagents used were of highest analytical grade available.

Method:

Cells are plated with a density of 5000 cells/well in 384-well poly-D-lysin plates and incubated for 1 day at 37° C., 5% CO2 in DMEM medium, 10% FCS, 1×NEAA, Puromycin (0.5 µg/ml) and G418 (1 mg/ml). Then the medium is changed to a identical medium without FCS and containing Octanoate-BSA (final concentration 100 µM each) and compound in DMSO (final DMSO concentration 0.3%). After incubation for 5 hours acylghrelin in the medium is measured by ELISA.

The medium sample is diluted 1:25 in Elisa buffer, a 25 µl aliquot is transferred to a 384-well ELISA plate previously washed 4 times with 100 µL wash buffer, and 25 µl tracer-solution is added. After incubation overnight (~20 h) at 4° C. temperature the plate is washed 4 times with 100 µl wash-buffer per well. Finally 50 µl Ellman's reagent is added to each well and the plate is incubated in the dark for 20 minutes. The absorbance is measured at 405 nm in an Envision multilabel reader and the amount of acylated ghrelin is calculated according to a acylated ghrelin standard curve provided in the same plate.

Each assay plate contains wells with vehicle controls (1% DMSO) for the measurement of non-inhibited transfer reaction (=100% Ctl) and wells with 10 µM ([Dap3]-Ghrelin) as controls for fully inhibited GOAT enzyme The analysis of the data is performed by calculation of the percentage of acyl-ghrelin produced in the presence of test compound compared to the amount of acyl-ghrelin produced in the vehicle control samples. An inhibitor of the GOAT enzyme will give values between 100% CTL (no inhibition) and 0% CTL (complete inhibition).

IC50 values are calculated with Assay Explorer or other suited software based on curve fitting of results of 8 different compound concentrations.

Results:

| example | IC50 [nM] |
|---------|-----------|
| 1.1 | 1.3 |
| 1.2 | 3.6 |
| 1.3 | 4.1 |
| 1.4 | 0.56 |
| 1.5 | 0.43 |
| 1.6 | 1.9 |
| 1.7 | 0.56 |
| 1.8 | 1.4 |
| 1.9 | 1.1 |
| 1.10 | 1.2 |
| 1.11 | 5.0 |
| 1.12 | 7.0 |
| 1.13 | 5.2 |
| 2.1 | 5.7 |
| 2.2 | 0.64 |
| 2.3 | 4.2 |
| 2.4 | 1.8 |
| 2.5 | 6.5 |
| 2.6 | 0.49 |
| 3.1 | 7.4 |
| 3.2 | 2.2 |
| 3.3 | 1.7 |
| 3.4 | 1.3 |
| 3.5 | 4 |

In view of their ability to modulate the activity of ghrelin O-acyl transferase (GOAT), in particular an inhibitory activity, the compounds of general formula I according to the invention, including the corresponding salts thereof, are suitable for the treatment of all those diseases or conditions which may be affected or which are mediated by the inhibition of ghrelin O-acyl transferase (GOAT).

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the inhibition of ghrelin O-acyl transferase (GOAT) in a patient, preferably in a human.

In yet another aspect the present invention relates to a method for treating a disease or condition mediated by the inhibition of ghrelin O-acyl transferase (GOAT) in a mammal that includes the step of administering to a patient, preferably a human, in need of such treatment a therapeutically effective amount of a compound or a pharmaceutical composition of the present invention.

Diseases and conditions mediated by inhibitors of ghrelin O-acyl transferase (GOAT) embrace obesity, including, but not limited to obesity in patients suffering from Prader-Willi-Syndrome (PWS), body weight regain, diabetes, particularly type 2 diabetes mellitus, insulin resistance, hyperphagia in PWS, Binge eating disorder, nighttime eating syndrome and alcohol and/or narcotic dependence.

Preferably, the compounds of the invention are used for treating obesity, body weight regain, type 2 diabetes, insulin resistance, and hyperphagia and obesity in PWS.

More preferably, the compounds of the invention are used for treating obesity, body weight regain, type 2 diabetes and insulin resistance.

In particular, the compounds and pharmaceutical compositions according to the invention are suitable for the treatment of obesity, including, but not limited to obesity in patients suffering from Prader-Willi-Syndrome, body weight regain, diabetes, in particular type 2 diabetes mellitus, and insulin resistance.

The compounds according to the invention are most particularly suitable for treating obesity.

The present invention further provides a GOAT inhibitor of the invention for use in a method of medical treatment.

GOAT inhibitors are useful, inter alia, in the reduction of food intake, promotion of weight loss, and inhibition or reduction of weight gain. As a result, they may be used for treatment of a variety of conditions, diseases, or disorders in a subject, including, but not limited to, obesity and various obesity-related conditions, diseases, or disorders, such as diabetes (e.g. type 2 diabetes). It will be understood that the GOAT inhibitors may thus be administered to subjects affected by conditions characterised by inadequate control of appetite or otherwise over-feeding, such as binge-eating disorder and Prader-Willi syndrome.

Thus, the invention provides a GOAT inhibitor of the invention for use in a method of treating, inhibiting or reducing weight gain, promoting weight loss and/or reducing excess body weight. Treatment may be achieved, for example, by control of appetite, feeding, food intake, calorie intake and/or energy expenditure.

The invention also provides a GOAT inhibitor of the invention for use in a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility.

The invention also provides a GOAT inhibitor of the invention for use in a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart (including diabetic cardiomyopathy and heart failure as a diabetic complication) coronary heart disease, peripheral artery disease or stroke.

The invention also provides a GOAT inhibitor of the invention for use in a method of lowering circulating LDL levels and/or increasing HDL/LDL ratio.

Effects of GOAT inhibitors on these conditions may be mediated in whole or in part via an effect on body weight, or may be independent thereof.

The invention further provides use of a GOAT inhibitor of the invention in the manufacture of a medicament for treating, inhibiting or reducing weight gain, promoting weight loss and/or reducing excess body weight.

The invention also provides use of a GOAT inhibitor of the invention in the manufacture of a medicament for treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility.

The invention also provides use of a GOAT inhibitor of the invention in the manufacture of a medicament for the prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart (including diabetic cardiomyopathy and heart failure as a diabetic complication) coronary heart disease, peripheral artery disease or stroke.

The invention also provides use of a GOAT inhibitor of the invention in the manufacture of a medicament for lowering circulating LDL levels and/or increasing HDL/LDL ratio.

The invention further provides a method of treating, inhibiting or reducing weight gain, promoting weight loss and/or reducing excess body weight in a subject, comprising administering a therapeutically effective amount of a GOAT inhibitor of the invention to the subject.

The invention also provides a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility in a subject, comprising administering a therapeutically effective amount of a GOAT inhibitor of the invention to the subject.

The invention also provides a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart (including diabetic cardiomyopathy and heart failure as a diabetic complication) coronary heart disease, peripheral artery disease or stroke in a subject, comprising administering a therapeutically effective amount of a GOAT inhibitor of the invention to the subject.

The invention further provides a method of lowering circulating LDL levels and/or increasing HDL/LDL ratio in a subject, comprising administering a therapeutically effective amount of a GOAT inhibitor of the invention to the subject.

The invention further provides the use of a GOAT inhibitor as described above in a method of cosmetic (i.e. non-therapeutic) weight loss. It will be understood that references to therapeutic uses of GOAT inhibitors and methods comprising administration of GOAT inhibitors may equally be taken to encompass uses and administration of such compositions.

Further aspects and embodiments of the present invention will become apparent from the disclosure below.

The dose range of the compounds of general formula I applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

A compound of the invention may be administered as part of a combination therapy together with another active agent for the treatment of the disease or disorder in question, e.g. an anti-diabetic agent, an anti-obesity agent, an agent for treatment of metabolic syndrome, an anti-dyslipidemia agent, an anti-hypertensive agent, a proton pump inhibitor, or an anti-inflammatory agent. In such cases, the two active agents may be given together or separately, e.g. as constituents in the same pharmaceutical composition or formulation, or as separate formulations.

Thus a compound of the invention may have some benefit if administered in combination with an anti-diabetic agent of known type, including, but not limited to, metformin, a sulfonylurea, a glinide, a DPP-IV inhibitor, a glitazone, a GLP-1 receptor agonist (including GLP-1 or a GLP-1 analogue, an exendin-4 or an exendin-4 analogue, any other GLP-1 receptor agonist including liraglutide (Saxenda™, Victoza™), Dulaglutide or Albiglutide or a glucagon-GLP-1 dual agonist, e.g. as described in WO2008/101017, WO2008/152403, WO2010/070252, WO2010/070253, WO2010/070255, WO2010/070251, WO2011/006497, WO2011/160630, WO2011/160633, WO2013/092703, WO2014/041195), an SGLT2 inhibitor (i.e. an inhibitor of sodium-glucose transport, e.g. a gliflozin such as empagliflozin, canagliflozin, dapagliflozin or ipragliflozin), a GPR40 agonist (FFAR1/FFA1 agonist, e.g. fasiglifam), or an insulin or an insulin analogue. Examples of appropriate insulin analogues include, but are not limited to, Lantus™, Novorapid™, Humalog™, Novomix™, Actraphane™ HM, Levemir™ Degludec™ and Apidra™. Other relevant anti-diabetic agents in this connection include GLP-1 receptor agonists, such as exenatide (Byetta™ and Bydureon™ exendin-4) and Byetta LAR™, lixisenatide (Lyxumia™) and liraglutide (Victoza™)

Moreover, a compound of the invention may be used in combination with an anti-obesity agent of known type, including, but not limited to, peptide YY or an analogue thereof, neuropeptide Y (NPY) or an analogue thereof, a cannabinoid receptor 1 antagonist, a lipase inhibitor, Human prolslet Peptide (HIP), a melanocortin receptor 4 agonist, a GLP-1 receptor agonist (including GLP-1 or a GLP-1 analogue, an exendin-4 or an exendin-4 analogue, any other GLP-1 receptor agonist including liraglutide (Saxenda™, Victoza™), Dulaglutide or Albiglutide or a glucagon-GLP-1 dual agonist, e.g. as described in WO2008/101017, WO2008/152403, WO2010/070252, WO2010/070253, WO2010/070255, WO2010/070251, WO2011/006497, WO2011/160630, WO2011/160633, WO2013/092703, WO2014/041195), Orlistat™ Sibutramine™, phentermine, a melanin concentrating hormone receptor 1 antagonist, CCK, amylin, pramlintide and leptin, as well as analogues thereof.

A compound of the invention may further be used in combination with an anti-hypertension agent of a known type, including, but not limited to, an angiotensin-converting enzyme inhibitor, an angiotensin II receptor blocker, a diuretic, a beta-blocker and a calcium channel blocker.

A compound of the invention may still further be used in combination with an anti-dyslipidemia agent of known type, including, but not limited to, a statin, a fibrate, a niacin, a PSCK9 (Proprotein convertase subtilisin/kexin type 9) inhibitor, and a cholesterol absorption inhibitor.

A compound of the invention may also be used in combination with a proton pump inhibitor (i.e. a pharmaceutical agent possessing pharmacological activity as an inhibitor of $H^+/K^+$-ATPase) of known type, including, but not limited to, an agent of the benzimidazole derivative type or of the imidazopyridine derivative type, such as Omeprazole™, Lansoprazole™, Dexlansoprazole™, Esomeprazole™ Pantoprazole™, Rabeprazole™, Zolpidem™, Alpidem™, Saripidem™ or Necopidem™.

In addition, with regard to anti-inflammatory treatment, a compound of the invention may be beneficial if administered in combination with an anti-inflammatory agent of known type, including, but not limited to:
steroids and corticosteroids, such as beclomethasone, methylprednisolone, betamethasone, prednisone, dexamethasone, and hydrocortisone;
non-steroidal anti-inflammatory agents (NSAIDs), such as propionic acid derivatives (e.g. alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives (e.g. indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac); fenamic acid derivatives (e.g. flufenamic acid, meclofenamic acid, mefenamic acid, niflumic acid and tolfenamic acid); biphenylcarboxylic acid derivatives (e.g. diflunisal and flufenisal); oxicams (e.g. isoxicam, piroxicam, sudoxicam and tenoxicam); salicylates (e.g. acetylsalicylic acid and sulfasalazine); and pyrazolones (e.g. apazone, bezpiperylon, feprazone, mofebutazone, oxyphenbutazone and phenylbutazone);

COX II inhibitors, such as rofecoxib and celecoxib; preparations of interferon beta (e.g. interferon beta-1a or interferon beta-1b);
and certain other compounds, such as 5-aminosalicylic acid and prodrugs and pharmaceutically acceptable salts thereof.

Metformin has also been demonstrated to have anti-inflammatory properties (see, e.g., Haffner et al., *Diabetes* 54: 1566-1572 (2005)) and as such may also be useful in combination with compounds of the invention.

The dosage for the combination partners mentioned above is usually ⅕ of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the inhibition of ghrelin O-acyl transferase (GOAT), in particular diseases or conditions as described hereinbefore and hereinafter.

In yet another aspect the present invention relates a method for treating a disease or condition mediated by the inhibition of ghrelin O-acyl transferase (GOAT) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

The following examples serve to further explain the invention without restricting it.

The hereinafter described compounds have been characterized through their characteristic mass after ionisation in a mass-spectrometer and/or their retention time on an analytical HPLC.
HPLC Methods:
Method 1:
 Column: Waters XBridge C18, 3×30 mm, 2.5 µm
 Detection: Agilent 1200 with DA- and MS-Detector
 Eluent A: Water (0.1% $NH_4OH$); Eluent B: Acetonitrile

| Gradient: | | | |
|---|---|---|---|
| Time (min.) | % Eluent B | Flow [mL/min] | Temp [° C.] |
| 0.00 | 3 | 2.2 | 60 |
| 0.20 | 3 | 2.2 | 60 |
| 1.20 | 100 | 2.2 | 60 |
| 1.25 | 100 | 3.0 | 60 |
| 1.40 | 100 | 3.0 | 60 |

Method 2:
 Column: Waters SunFire, 3×30 mm, 2.5 µm
 Detection: Agilent 1200 with DA- and MS-Detector
 Eluent A: Water (0.1% Trifluoroacetic acid); Eluent B: Acetonitrile

| Gradient: | | | |
|---|---|---|---|
| Time (min.) | % Eluent B | Flow [mL/min] | Temp [° C.] |
| 0.00 | 3 | 2.2 | 60 |
| 0.20 | 3 | 2.2 | 60 |
| 1.20 | 100 | 2.2 | 60 |
| 1.25 | 100 | 3.0 | 60 |
| 1.40 | 100 | 3.0 | 60 |

Method 3:
 Column: Waters SunFire C18, 3×30 mm, 2.5 µm
 Detection: Agilent 1200 with DA- and MS-Detector
 Eluent A: Water (0.1% Formic acid); Eluent B: Acetonitrile

| Gradient: | | | |
|---|---|---|---|
| Time (min.) | % Eluent B | Flow [mL/min] | Temp [° C.] |
| 0.00 | 3 | 2.2 | 60 |
| 0.20 | 3 | 2.2 | 60 |
| 1.20 | 100 | 2.2 | 60 |
| 1.25 | 100 | 3.0 | 60 |
| 1.40 | 100 | 3.0 | 60 |

Preparation of the Examples

Method 1

Intermediate 1.1.A

7-Amino-5-methyl-[1,2,5]oxadiazolo[3,4-b]pyridin-6-carboxylic Acid Ethyl Ester

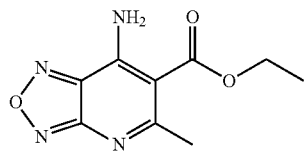 [SMILES: CCOC(=O)c1c(C)nc2nonc2c1N]

4-Amino-1,2,5-oxadiazole-3-carbonitrile (1.00 g; 9.08 mmol) and ethyl acetoacetate (1.15 mL; 9.08 mmol) are dissolved in 10 mL toluene. Tin(IV)chloride (2.13 mL; 18.2 mmol) is added and the mixture is stirred at reflux for 30 minutes. The mixture is evaporated and the residue is taken up in NaHCO$_3$ (half saturated aqueous solution) and extracted two times with dichloro methane. The combined organic layers are dried and concentrated under reduced pressure.

Yield: 2.47 g (98% of theory)
Mass spectrometry (ESI$^+$): m/z=223 [M+H]$^+$
HPLC (Method 1): Retention time=0.853 min.

Intermediate 1.1.B (7-Amino-5-methyl-[1,2,5]oxadiazolo[3,4-b]pyridin-6-yl)-methanol

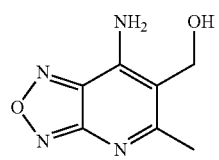

The reaction is carried out under an argon atmosphere. A mixture of 7-amino-5-methyl-[1,2,5]oxadiazolo[3,4-b]pyridin-6-carboxylic acid ethyl ester (1.00 g; 3.60 mmol) in 10 mL toluene and 5 mL tetrahydrofuran is cooled to −78° C. Sodium bis(2-methoxy ethoxy)aluminium hydride (65% in toluene; 1.13 mL; 3.78 mmol) is added and the mixture is allowed to warm up to room temperature. After stirring over night at room temperature sodium bis(2-methoxy ethoxy) aluminium hydride (65% in toluene; 1.13 mL; 3.78 mmol) is added. After stirring for further 1.5 hours the mixture is diluted with sodium potassium-tartrate (saturated aqueous solution) and extracted two times with tetrahydrofuran/ethyl acetate. The combined organic layers are dried and concentrated under reduced pressure. The residue is purified by reverse phase chromatography-HPLC (modifier: trifluoroacetic acid).

Yield: 530 mg (81% of theory)
HPLC (Method 3): Retention time=0.239 min.

Intermediate 1.1.C

6-Chloromethyl-5-methyl-[1,2,5]oxadiazolo[3,4-b]pyridin-7-ylamine

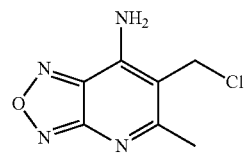

To (7-amino-5-methyl-[1,2,5]oxadiazolo[3,4-b]pyridin-6-yl)-methanol (30.0 mg; 0.17 mmol) in 0.2 mL N,N-dimethylformamide are added dropwise thionylchloride (24.2 µL; 0.33 mmol and the mixture is stirred for 20 minutes at room temperature. The mixture is evaporated and further used as crude product.

Yield: 33.0 mg (100% of theory)
HPLC (Method 2): Retention time=0.281 min.

Example 1.1 6-{[4-(Difluoromethyl)piperidin-1-yl]methyl}-5-methyl-[1,2,5]oxadiazolo[3,4-b]pyridin-7-amine

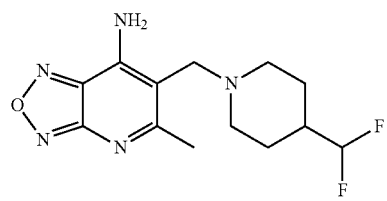 [SMILES: Cc1nc2nonc2c(N)c1CN1CCC(C(F)F)CC1]

To 4-(difluoromethyl)piperidine hydrochloride (51 mg; 0.30 mmol) in 0.5 mL N-methylpyrrolidine are added N,N-diisopropylethylamine (130 µL; 0.76 mmol) and stirred for a few minutes. Intermediate 1.1.C (6-(Chloromethyl)-5-methyl-[1,2,5]oxadiazolo[3,4-b]pyridin-7-amine, 50 mg; 0.25 mmol) dissolved in 3 mL tetrahydrofuran is added dropwise and the mixture is stirred for 2 hours. The reaction is quenched with acetonitrile and purified by reverse phase chromatography-HPLC (modifier: ammonium hydroxide).

Yield: 27 mg (36% of theory)
Mass spectrometry (ESI$^+$): m/z=298 [M+H]$^+$
HPLC (Method 1): Retention time=0.941 min.

Analogously to Example 1.1 the following examples are prepared using Intermediate 1.1.C (6-(chloromethyl)-5-methyl-[1,2,5]oxadiazolo[3,4-b]pyridin-7-amine) and the corresponding substituted heterocyclic amine derivative:

| Ex. | Structure | Mass spectrometry | HPLC Retention time |
|---|---|---|---|
| 1.2 | 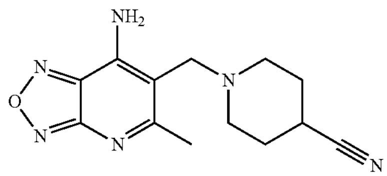 [SMILES: Cc1nc2nonc2c(N)c1CN1CCC(C#N)CC1] | (ESI+): m/z = 273 [M + H]+ | (Method 1): 0.806 min. |
| 1.3 | 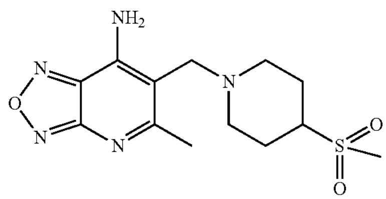 [SMILES: Cc1nc2nonc2c(N)c1CN1CCC(S(C)(=O)=O)CC1] | (ESI+): m/z = 326 [M + H]+ | (Method 1): 0.716 min. |
| 1.4 | 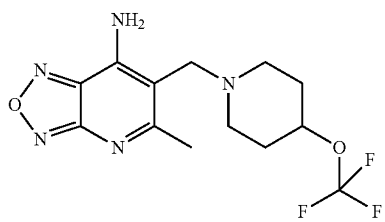 [SMILES: Cc1nc2nonc2c(N)c1CN1CCC(OC(F)(F)F)CC1] | (ESI+): m/z = 332 [M + H]+ | (Method 1): 1.010 min. |
| 1.5 | 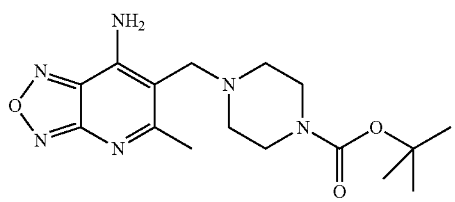 [SMILES: Cc1nc2nonc2c(N)c1CN1CCN(C(=O)OC(C)(C)C)CC1] | (ESI+): m/z = 349 [M + H]+ | (Method 1): 0.973 min. |
| 1.6 | 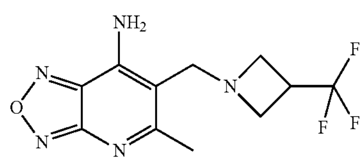 [SMILES: Cc1nc2nonc2c(N)c1CN1CC(C(F)(F)F)C1] | (ESI+): m/z = 288 [M + H]+ | (Method 5): 0.73 min. |
| 1.7 | 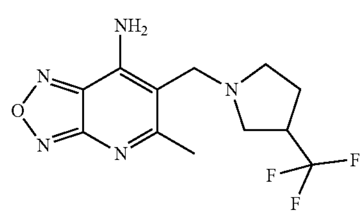 [SMILES: Cc1nc2nonc2c(N)c1CN1CCC(C(F)(F)F)C1] | (ESI+): m/z = 302 [M + H]+ | (Method 5): 0.79 min. |
| 1.8 | 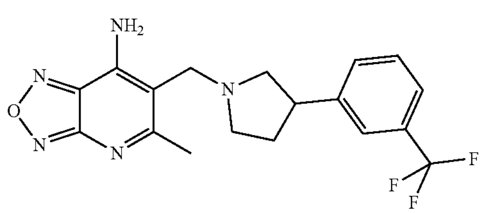 [SMILES: Cc1nc2nonc2c(N)c1CN1CCC(c2cccc(C(F)(F)F)c2)C1] | (ESI+): m/z = 378 [M + H]+ | (Method 5): 0.97 min. |
| 1.9 | 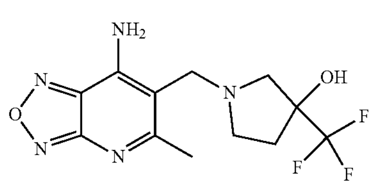 [SMILES: Cc1nc2nonc2c(N)c1CN1CCC(O)(C(F)(F)F)C1] | (ESI+): m/z = 318 [M + H]+ | (Method 5): 0.64 min. |

| Ex. | Structure | Mass spectrometry | HPLC Retention time |
|---|---|---|---|
| 1.10 | ![structure] | (ESI+): m/z = 341 [M + H]+ | (Method 5): 0.68 min. |
| 1.11 | ![structure] | (ESI+): m/z = 292 [M + H]+ | (Method 5): 0.63 min. |
| 1.12 | ![structure] | (ESI+): m/z = 270 [M + H]+ | (Method 5): 0.37 min. |
| 1.13 | ![structure] | (ESI+): m/z = 327 [M + H]+ | (Method 3): 0.564 min. |

Method 2

Intermediate 2.1.A

5-Methyl-6-[(piperazin-1-yl)methyl]-[1,2,5]oxadiazolo[3,4-b]pyridin-7-amine Trihydrochloride

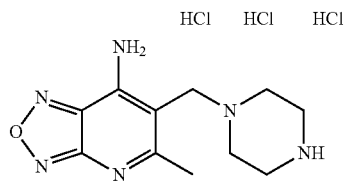 [SMILES: Cl ; Cl ; Cl ; Cc1nc2nonc2c(N)c1CN1CCNCC1]

Example 1.5 (tert-Butyl 4-({7-amino-5-methyl-[1,2,5]oxadiazolo[3,4-b]pyridin-6-yl}methyl)piperazine-1-carboxylate, 2.85 g; 8.18 mmol) is dissolved in 50 mL dioxane and hydrochlorid acid (4 M in dioxane) (5.37 mL; 21.31 mmol) are added and the mixture is stirred over night at room temperature. The reaction mixture is stirred for 4.5 hours at 70° C. 50 mL water is added and the reaction is stirred over night at room temperature and 3.5 hours at 90° C. The mixture is concentrated and the residue is lyophilized.

Yield: 2.9 g (99% of theory)
Mass spectrometry (ESI+): m/z=349 [M+H]+
HPLC (Method 2): Retention time=0.718 min.

Example 2.1

1-[4-({7-Amino-5-methyl-[1,2,5]oxadiazolo[3,4-b]pyridin-6-yl}methyl)piperazin-1-yl]-2,2,2-trifluoro-ethan-1-one

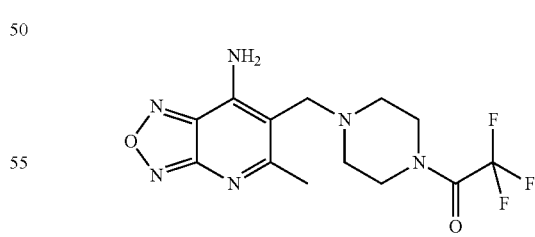

Intermediate 2.1.A (5-Methyl-6-[(piperazin-1-yl)methyl]-[1,2,5]oxadiazolo[3,4-b]pyridin-7-amine trihydrochloride) is suspended in 5 mL dichloromethane and N-ethyldiisopropyllamine (0.674 mL; 3.95 mmol) is added. Trifluoroacetic anhydride (0.165 mL; 1.18 mmol) is added dropwise at 0° C. The reaction is allowed to warm up to room temperature over night. The mixture is concentrated, acidified with trifluoroacetic acid and purified by reverse phase chromatography-HPLC (modifier: trifluoroacetic acid).

Yield: 42 mg (12% of theory)
Mass spectrometry (ESI⁺): m/z=345 [M+H]⁺
HPLC (Method 2): Retention time=0.682 min.

Analogously to Example 2.1 the following examples are prepared using Intermediate 2.1.A (5-Methyl-6-[(piperazin-1-yl)methyl]-[1,2,5]oxadiazolo[3,4-b]pyridin-7-amine trihydrochloride) and the corresponding sulfonyl chloride, carbonyl chloride or carbono chloridate:

| Ex. | Structure | Mass spectrometry | HPLC Retention time |
|---|---|---|---|
| 2.2 | 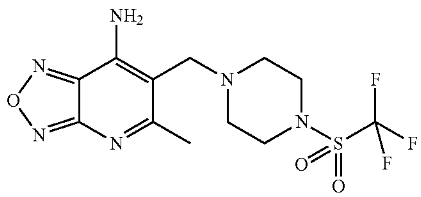 [SMILES: Cc1nc2nonc2c(N)c1CN1CCN(S(=O)(=O)C(F)(F)F)CC1] | (ESI⁺): m/z = 381 [M + H]⁺ | (Method 2): 0.833 min. |
| 2.3 | 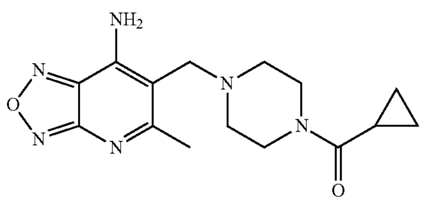 [SMILES: Cc1nc2nonc2c(N)c1CN1CCN(C(=O)C2CC2)CC1] | (ESI⁺): m/z = 317 [M + H]⁺ | (Method 2): 0.408 min. |
| 2.4 | 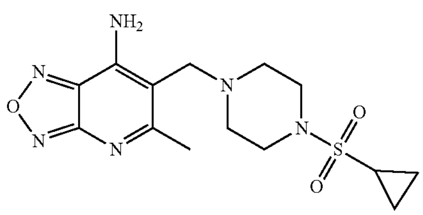 [SMILES: Cc1nc2nonc2c(N)c1CN1CCN(S(=O)(=O)C2CC2)CC1] | (ESI⁺): m/z = 353 [M + H]⁺ | (Method 2): 0.556 min. |
| 2.5 | 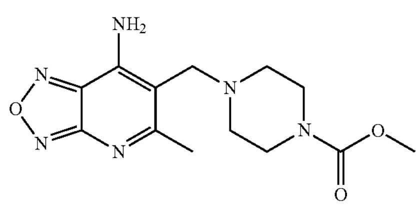 [SMILES: COC(=O)N1CCN(Cc2c(C)nc3nonc3c2N)CC1] | (ESI⁺): m/z = 307 [M + H]⁺ | (Method 2): 0.339 min. |
| 2.6 | 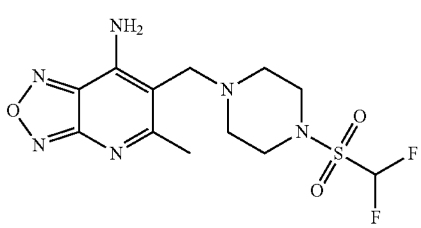 [SMILES: Cc1nc2nonc2c(N)c1CN1CCN(S(=O)(=O)C(F)F)CC1] | (ESI⁺): m/z = 363 [M + H]⁺ | (Method 2): 0.614 min. |

Method 3

Example 3.1

6-(3,3-Difluoro-piperidin-1-ylmethyl)-5-methyl-[1,2,5]oxadiazolo[3,4-b]pyridin-7-ylamine

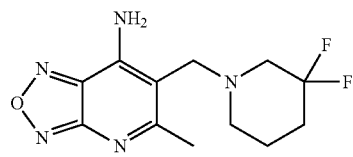 [SMILES: Cc1nc2nonc2c(N)c1CN1CCCC(F)(F)C1]

To 3,3-difluoro-piperidine hydrochloride (47.6 mg; 0.302 mmol) and N,N-diisopropylethylamine (65.3 µl; 0.378 mmol) in 0.5 mL N-methylpyrrolidinone is added Intermediate 1.1.C (6-Chloromethyl-5-methyl-[1,2,5]oxadiazolo[3,4-b]pyridin-7-ylamine, 50 mg; 252 mmol) and the reaction mixture is stirred for 1 hour. Additional 3,3-difluoro-piperidine hydrochloride (47.6 mg; 0.302 mmol) and N,N-diisopropylethylamine (65.3 p; 0.378 mmol) are added the reaction mixture is stirred for 2.5 hours. The reaction mixture is purified by reverse phase chromatography-HPLC (modifier: NH$_4$OH).

Yield: 13 mg (16% of theory)

Mass spectrometry (ESI$^+$): m/z=284 [M+H]$^+$

HPLC (Method 1): Retention time=0.908 min.

5-Methyl-6-(4-trifluoromethyl-piperidin-1-ylmethyl)-[1,2,5]oxadiazolo[3,4-b]pyridin-7-ylamine

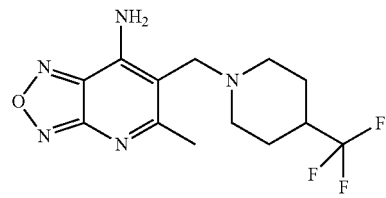 [SMILES: Cc1nc2nonc2c(N)c1CN1CCC(C(F)(F)F)CC1]

To 4-trifluoromethyl-piperidine hydrochloride (95.5 mg; 0.503 mmol) and caesium carbonate (328 mg; 1.01 mmol) in 1.5 mL N-methylpyrrolidinone Intermediate 1.1C (6-Chloromethyl-5-methyl-[1,2,5]oxadiazolo[3,4-b]pyridin-7-ylamine, 50 mg; 252 mmol) is added and the reaction mixture is stirred for 1 hour. The mixture is purified by reverse phase chromatography-HPLC (modifier: NH$_4$OH).

Yield: 13 mg (16% of theory)

Mass spectrometry (ESI$^+$): m/z=316 [M+H]$^+$

HPLC (Method 1): Retention time=1.009 min.

Analogously to Example 3.1 the following examples are prepared using Intermediate 1.1.C (6-(chloromethyl)-5-methyl-[1,2,5]oxadiazolo[3,4-b]pyridin-7-amine) and the corresponding substituted heterocyclic amine derivative:

| Ex. | Structure | Mass spectrometry | HPLC Retention time |
|---|---|---|---|
| 3.2 | ![structure] | (ESI$^+$): m/z = 284 [M + H]$^+$ | (Method 1): 0.906 min. |
| 3.3 | ![structure] | (ESI$^+$): m/z = 316 [M + H]$^+$ | (Method 1): 1.012 min. |
| 3.4 | ![structure] | (ESI$^+$): m/z = 316 [M + H]$^+$ | (Method 1): 1.009 min. |
| 3.5 | ![structure] | (ESI$^+$): m/z = 358 [M + H]$^+$ | (Method 1): 1.002 min. |

The invention claimed is:
1. A compound of formula

(I)

wherein
a) if p is 1 and q is 1, then X is $C(R^2)_2$, O or $NR^3$; or
b) if p is 0 and q is 0, then X is $CHR^1$; or
c) if p is 1 and q is 0, then X is $CR^1R^2$;
and, in any of the above-mentioned cases,
n is an integer selected from the group consisting 0, 1, and 2;
$R^1$ is independently selected from the group consisting of H, F, CN, $C_{1-3}$-alkyl and phenyl,
wherein any alkyl group is optionally substituted with 1 or more F atoms, and
wherein the phenyl group is optionally substituted with 1 or more F atoms or with one $CF_3$ group;
$R^2$ is independently selected from the group consisting of H, F, CN, $C_{1-3}$-alkyl, —OH, —O—$C_{1-4}$-alkyl, —O-pyridinyl and —$SO_2$—($C_{1-3}$-alkyl),
wherein each alkyl group is optionally substituted with 1 or more F atoms or with one OH group, and
wherein the pyridinyl group is optionally substituted with a $CH_3$ group; and
$R^3$ is selected from the group consisting of —$SO_2$—($C_{1-3}$-alkyl), —$SO_2$—($C_{3-7}$-cycloalkyl), —C(=O)—($C_{1-3}$-alkyl), —C(=O)—($C_{3-7}$-cycloalkyl), —C(=O)—O—($C_{1-6}$-alkyl), and $C_{1-3}$-alkyl,
wherein each alkyl group is optionally substituted with 1 or more F atoms;
wherein each of the above-mentioned alkyl groups may be substituted with one or more F;
or a salt thereof.

2. The compound of formula (I) according to claim 1, wherein
either p is 1 and q is 1 and X is $C(R^2)_2$, O or $NR^3$; or p is 1 and q is 0 and X is $CR^1R^2$;
and, in both of the above-mentioned cases,
n is 0 or 1; and
$R^1$ is H, F, methyl or phenyl,
wherein the methyl group is optionally substituted with 1 to 3 F atoms,
and wherein the phenyl group is optionally substituted with 1 to 3 F atoms or with one $CF_3$ group;
the groups $R^2$ are independently of each other selected from the group consisting of H, F, CN, $CH_3$, —CH$(CH_3)_2$, OH, —O—$CH_3$, —O-pyridin-4-yl and —$SO_2$—$CH_3$,
wherein each $CH_3$ group is optionally substituted with 1 to 3 F atoms,
and wherein the isopropyl group is optionally substituted with one OH group,
and wherein the pyridinyl group is optionally substituted with 1 $CH_3$ group; and
$R^3$ is —$SO_2$—$CH_3$, —$SO_2$-cyclopropyl, —C(=O)—$CH_3$, —C(=O)-cyclopropyl or —C(=O)—O—($C_{1-4}$-alkyl),
wherein each alkyl group is optionally substituted with 1 to 3 F atoms.

3. The compound of formula (I) according to claim 1, wherein p and q are each 1.

4. The compound according to claim 3 having formula (I.1)

wherein
X is selected from the group consisting of $C(R^2)_2$ and $NR^3$;
n is 0;
the groups $R^2$ are independently selected from the group consisting of: H, F, CN, $CH_3$, $CHF_2$, $CF_3$, —O—$CF_3$ and —$SO_2$—$CH_3$; and
$R^3$ is selected from the group consisting of —$SO_2$—$CH_3$, —$SO_2$—$CHF_2$, —$SO_2$—$CF_3$, —$SO_2$-cyclopropyl, —C(=O)—$CF_3$, —C(=O)-cyclopropyl, —C(=O)—O—$CH_3$ and —C(=O)—O—$(C(CH_3)_3)$;
or a salt thereof.

5. The compound according to claim 1 having the formula (I.11)

wherein
$R^1$ is selected from the group consisting of H, F, $CF_3$ and 3-trifluoro-phenyl; and
$R^2$ is selected from the group consisting of H, F, $CF_3$, —C(OH)($CH_3)_2$, OH and —O-(2-methyl-pyridin-4-yl);
with the proviso that at least one of $R^1$ and $R^2$ is not H;
or a salt thereof, particularly a pharmaceutically acceptable salt thereof.

6. The compound according to claim 1 having the formula or a salt thereof.

7. A pharmaceutically acceptable salt of a compound according to claim 1.

8. A method for treating obesity, type 2 diabetes mellitus, and/or insulin resistance in patients suffering from Prader-Willi-Syndrome, the method comprising administering a pharmaceutically effective amount of a compound according to claim 1, or a pharmaceutically acceptable salt thereof, to a patient in need thereof.

9. A pharmaceutical composition comprising a compound according to claim 1, or a pharmaceutically acceptable salt thereof, optionally together with one or more inert carriers and/or diluents.

10. A method for treating a disease or condition which is mediated by inhibiting the activity of the ghrelin O-acyl transferase (GOAT), the method comprising administering a pharmaceutically effective amount of a compound according to claim 1, or a pharmaceutically acceptable salt thereof, to a patient in need thereof.

11. A pharmaceutical composition comprising one or more compounds according to claim 1, or a pharmaceutically acceptable salt thereof, and one or more additional therapeutic agents, optionally together with one or more inert carriers and/or diluents.

12. The compound according to claim 6, wherein said compound is:

13. The compound according to claim 6, wherein said compound is:

14. The compound according to claim 6, wherein said compound is:

15. The compound according to claim 6, wherein said compound is:

16. The compound according to claim 6, wherein said compound is:

* * * * *